United States Patent [19]

Homsy

[11] 3,992,725
[45] Nov. 23, 1976

[54] IMPLANTABLE MATERIAL AND APPLIANCES AND METHOD OF STABILIZING BODY IMPLANTS

[76] Inventor: Charles A. Homsy, 11526 Raintree Circle, Houston, Tex. 77024

[22] Filed: Oct. 17, 1974

[21] Appl. No.: 515,443

Related U.S. Application Data

[63] Continuation-in-part of Ser. No. 416,641, Nov. 16, 1973, abandoned, which is a continuation of Ser. No. 145,497, May 20, 1971, abandoned.

[52] U.S. Cl. ............................................ 3/1; 3/1.9; 3/1.91; 128/92 C; 32/10 A; 428/288; 428/408; 428/422; 264/56
[51] Int. Cl.² ............................................ A61F 1/24
[58] Field of Search .................... 3/1, 1.9–1.913; 128/92 C, 92 CA, 1 R; 32/10 A; 161/170, 159, 162, 168, 169, 189, 156; 428/288, 408, 422

[56] References Cited
UNITED STATES PATENTS

| | | | |
|---|---|---|---|
| 3,314,420 | 4/1967 | Smith et al. | 128/92 C |
| 3,609,867 | 10/1971 | Hodosh | 32/10 A |
| 3,662,405 | 5/1972 | Bortz et al. | 3/1.9 |
| 3,893,196 | 7/1975 | Hochman | 3/1.91 |

FOREIGN PATENTS OR APPLICATIONS

| | | | |
|---|---|---|---|
| 1,902,700 | 8/1970 | Germany | 3/1.91 |

OTHER PUBLICATIONS
"Quartz & Graphite Filament Reinforced Polymer Composites for Orthopedic Surgical Application," by S. Musikant, *Journal of Biomedical Materials Research Symposium*, vol. 1, pp. 225–235, Jan. 1971.

*Primary Examiner*—Ronald L. Frinks
*Attorney, Agent, or Firm*—Vinson, Elkins, Searls, Connally & Smith

[57] ABSTRACT

A composition of material suitable for in vivo implantation to provide an environment in which normal tissue growth is fostered which composition is a porous fibrous structure in which the critical surface tension of the fibers is 35 dynes per centimeter or higher. This composition in the preferred form is a porous structure of carbon or graphite fibers bonded together by sintered polytetrafluoroethylene in a manner to expose a maximum amount of fiber surface.

Another composition of material suitable for implantation for wear surfaces includes carbon fibers and polytetrafluoroethylene resin and is processed to align the carbon fibers with the wear surfaces. The method of preparing both material includes the step of mixing, filtering, compressing, rolling, sintering and drying. The method of stabilizing appliances or implants includes bonding the ingrowth material to the appliance or implant. Also the combination of the ingrowth material with appliances, tendon replacement elements and wear material are included.

35 Claims, No Drawings

IMPLANTABLE MATERIAL AND APPLIANCES AND METHOD OF STABILIZING BODY IMPLANTS

The present application is a continuation-in-part application of my prior copending application Ser. No. 416,641, filed Nov. 16, 1973, now abandoned which application is a continuation application of my prior copending application Ser. No. 145,497, filed May 20, 1971, now abandoned.

SUMMARY

The present invention relates to a composition of material which when implanted in a body promotes ingrowth of the normal body tissue, to the method of producing such material, to the method, of stabilizing prosthetic appliances and promoting ingrowth of tissue, to the appliances with the ingrowth material bonded thereto, to the tendon replacements with the ingrowth material bonded at each end for securing the tendon replacement, to an implantable wear material and to the combination of the ingrowth material bonded to the wear material.

Prior implantable materials have been such that they are normally sequestered in a fibrous tissue. None of such prior materials have had the characteristic of promoting normal tissue growth but such materials have inhibited the ingrowth of normal body tissue.

An object of the present invention is to provide an improved implantable composition of material which promotes ingrowth of normal body tissue.

Another object is to provide an improved implantable material suitable for stabilizing metal prostheses.

A further object is to provide an improved implantable material for use in soft tissue augmentation.

Another object is to provide an improved composition of material suitable for use in orthopedic rebuilding of joints and parts thereof.

A still further object is to provide an improved method of making an implantable composition of material.

Still another object of the present invention is to provide an improved composition of material suitable for implantation which may be sterilized by the usual steam autoclave procedures without being adversely effected thereby.

Another object is to provide an improved implantable composition of material which promotes ingrowth of tissue and is not sequestered by fibrous tissue when implanted.

Another object is to provide an implantable material suitable for implantation in a joint in that it is highly wear resistant and has low friction properties.

A further object is to provide a method of promoting ingrowth of tissues for soft tissue augmentation, for stabilization of implants and for other purposes wherein such ingrowth of tissues is desirable.

These and other objects and advantages are hereinafter set forth and explained.

DESCRIPTION OF THE PREFERRED EMBODIMENTS

The preferred composition of material for tissue ingrowth consists of sintered polytetrafluoroethylene with carbon fibers and substantial void space defined therein. The polytetrafluoroethylene material has been used for implantable devices and has been found to be bio-compatible, that is, it does not produce any inflammatory response by the host tissue. The preferred material to be used is marketed by Du Pont Co. as Teflon TFE. This material has a low surface energy and, consequently, low affinity for tissue elements therefore would not normally be considered suitable to foster tissue ingrowth on implantation to any appreciable degree.

It has been discovered that with implanted materials the relative surface energy or wettability has an effect on the manner in which the tissue responds. Tissue element attachment to the surface of an implanted material can be substantially reduced by decreasing the surface energy or reducing the wettability. Such low surface energy materials are generally sequestered in fibrous tissue.

Since the polytetrafluoroethylene (hereinafter PTFE) material has low surface energy, the promotion of ingrowth of normal body tissues will be aided if the surface energy can be increased. Also, for such ingrowth the composition of material should contain substantial void space.

It is well known that cellular elements of tissue exhibit a degree of electrical polarity. Consequently electrostatic adhesion of cellular elements to the surface of an implanted material is minimized when the implanted material itself exhibits very low surface energy (low critical surface tension) that is, electrostatic attractive force. It has therefore been one of the objects of this invention to take advantage of the bio-compatibility of PTFE material and the polymeric properties of this material as these relate to the development of highly porous structures and at the same time recognize desirability of fostering tissue ingrowth and attachment to the implant material by providing a substantial surface area which exhibits a relatively high surface energy for electrostatic attraction of tissue elements. In the preferred form of the present invention this is achieved by incorporating substantial quantities of carbon or graphite surface tension of the order of 50 dynes per centimeter. In this way an implant structure is provided which presents to cellular and tissue elements, a substantial percentage of surface exhibiting relatively high critical surface tension.

The preferred composition of material of the present invention is made by intimately mixing in the proportions hereinafter set forth carbon fibers, and PTFE, either particles or fibers. Generally, it is preferred to use not more than 85% by volume of the carbon material. The preferred amounts of PTFE fibers to resin is preferred to be greater than 1 to 2 and less than 2 to 1. The PTFE fibers are preferred to have a strand length up to 2 inches.

In order to help provide the desired void space, a material which is soluble in a suitable solvent is added to the above mixture in an amount to produce the desired amount of void space in the material, preferably in the range from 60% to 90% of the volume of the finished material. If water is to be the solvent, the soluble material may be common material such as sodium chloride crystals of particle size between 10 and 600 microns.

Alternatively other soluble material/solvent combinations may be used. For example, when water is to be the solvent, soluble materials may be selected from the group of water soluble salts which are thermally stable at temperatures below about 700° F. Such salts could be sodium carbonate, calcium fluoride, magnesium sulphate, and others. It will generally be preferred to use the sodium chloride-water system since the sodium chloride would be completely compatible in the body in the event small amounts were left in the material from the leaching step hereinafter described.

The carbon material may be as indicated above carbon fibers. The carbon fibers are in strands up to 2 inches in length.

A typical formulation would include 80% sodium chloride, 10% carbon fibers, 6% PTFE resin fibers, and 4% PTFE particulate resin. Such formulation when prepared as herein set forth has been found to have rapid tissue ingrowth, and sufficient strength.

| carbon fibers | — | 4% to 20% by volume |
|---|---|---|
| resin fibers | — | 4% to 10% by volume |
| resin particles | — | 2% to 10% by volume |
| soluble material | — | 90% to 60% by volume |

The steps involved in preparing these materials are as follows:

a. Mixing: In this step the polymer and the carbon and soluble ingredients are suspended in a suitable organic solvent such as purified isoparaffinic solvent; it is preferred that aromatic content of such solvent be less than 1% by weight; the resulting slurry is mixed at very high speed in a high shear mixer such as a Waring blender. The proportion of solvent to dry ingredients is important and must be adjusted to the size of the mixer used. The total volume of our mixer is 1000 milliliters and 500 milliliters of solvent are used for dry ingredient weights of the order of 80 grams. Mixing is carried out for between one and five minutes depending upon the particular ingredients used.

b. Filtration: The mixed slurry is rapidly poured into a vacuum filter such as a Buchner funnel, and filtration proceeds from between a few seconds to several minutes depending upon ingredients used. The residual solvent left in the filter cake is carefully monitored so as to be less than about 20% by weight.

c. Compression: The filter cake from step (b) is placed within the platens of a heated press (150° F) and compression is applied at levels of between 50 to 3,000 pounds per square inch for between one and five minutes, again depending upon the particular ingredients. The present residual solvent in the filter cake after compression is routinely monitored and conditions are adjusted so that the level of solvent is between six and sixteen weight percent.

d. Rolling: The compressed filter cake from step (c) is run through the nip of heated rolls such that the thickness of the cake is reduced in decrements of approximately 20/1000 of an inch to levels of between 80 and 20/1000 of an inch depending upon the intended final thickness of the product. The temperature of the heated rolls should be in the range of 100° F through 280° F. That is, heated rolls over this temperature range are required in order to help volatilize the carrier solvent. Moreover, during this step each pass through the rolls is made perpendicular with the direction of the previous rolling maneuver.

e. Drying: Stock material is dried to evaporate any residual solvent by placing in an oven held at temperatures of between 150° F and 350° F for several hours — up to 48 hours usually.

f. Sintering: The dried stock is now sintered. Sintering is carried out in a heated press at temperatures between 610° F and 680° F and a pressure between 50 to 5000 pounds per square inch for periods of time from 1 to 30 minutes depending upon the thickness of stock. Alternately sintering may be carried out by heating the stock material to temperatures between 610° F and 680° F for periods extending to several hours.

g. Leaching: The stock is leached to dissolve out water soluble filler material by placement in a container containing distilled water and thereby develop discrete volume and porosity. Distilled water is caused to flow at a slow rate through such container in order to provide the maximum driving force for diffusion of dissolved filler from the stock into a leaching water. The leaching step is usually allowed to proceed for 48 hours for stock having a thickness of one-fourth of an inch. Longer times would probably be required for thicker stock. The distilled water is preferred to be warm to increase the rate of dissolving of salt.

h. Drying: The leach stock is then placed in an oven held at a temperature between about 160° F and 350° F in order to affect drying of the residual water contained within the stock material. The drying step may include a 24 hour hold at 300° F to volatilize any residual solvent.

The product material from the above series of steps exhibits several important properties of significance to tissue ingrowth. During the leaching step the voids are created in the material. A portion of the voids have a spheroidal shape as they are formed by the leaching of generally spheroidal sodium chloride crystals from the material. In addition, the material which is produced as described also develops dendritic voids which interconnect in random fashion with the spheroidal voids to thereby provide a particularly effective open structure for the ingress and egress of body fluids necessary for the development and maturation of tissue within the voids.

Further, the material immediately surrounding these voids has a relatively high surface tension of the graphite fibers since the structure formed does not coat the graphite fibers with the PTFE resin and fibers but provides adequate structure and bonding links to provide a material having structural integrity after the leaching step removes the soluble material.

It is believed that with the development and maturation of tissue within such voids, such tissue is not as vulnerable to infection as prior implants since substantial blood supply is developed to allow the normal body functions for fighting infection to be active within such material. In prior materials for implants, the appearance of an infection in connection with an implanted device generally necessitated the removal of the device if the normal body infection fighting mechanisms were not able to reach the infected area.

Additionally, because of the resiliency and distensibility of this composition of material, the tissues developing therein feel or are subjected to the normal mechanical forces at the sites of the implant which assist in the formation of the type of tissue needed at such location.

The improved composition of material, because its porosity may be preselected and because it promotes the ingrowth of normal body tissues, was initially considered for the stabilization of orthopedic prostheses.

Upon consideration of the promotion into the composition of material of ingrowth of body tissues, such composition of material appears to have other applications including soft tissue augmentation, partial and complete joint prostheses, birth control by vas or tube blockage from material implant, fixation of artifical teeth, tendon replacement and fixation, alveolar ridge augmentation and other implant procedures.

It has been found that the kind and porosity of the composition of material may be controlled by the amount of soluble filler and carbon fiber included in the original mixture. Also, the combination of carbon and PTFE is adjusted to provide a balance of mechanical behavior and surface energy.

In the formation of the material the rolling proceeds until the thickness of the material is of the order of one to two millimeters thick to thereby provide a maximum strength. When thicker stock is desired particularly for soft tissue and alveolar ridge augmentation it can be achieved by following the above steps (a), (b), (c), (d) and (e) and then stacking the dried stock to the desired multiple of the single ply thickness. The stacked layers are sandwiched between aluminum foil and placed within the platens of a press held at a temperature of 620° to 690° F. Pressure is applied gradually over one to two minutes depending on the area of the laminate to a final hold pressure of 1000 pounds per square inch. This hold pressure is maintained for a period of time equal to the number of layers times five minutes and may not need to exceed fifteen minutes. This laminated stock is then leached and dried as set forth in steps (g) and (h) above.

A specific preferred formulation includes graphite fiber sold by Carborundum Company under the name GY2F, 4.5 grams; bleached fibers of TEFLON TFE sold by Du Pont Company, 4.14 grams; Du Pont TEFLON TFE-6 resin 2.76 grams; and sodium chloride reagent grade crystal sold by J. T. Baker Laboratory Chemicals. (52.0 grams).

This preferred material has been shown to exhibit tensile stress strain behavior normally associated with low strength resilient structures. More specifically, the curve of imposed tensile stress versus percent elongation exhibits a linear region from the coordinate origin to stress levels of about 5 kg/cm$^2$ and about 10% elongation; thereafter, the slope of the curve diminishes gradually until a tensile stress of approximately 10 kg/cm$^2$ is imposed when rupture occurs. Ultimate elongation at this stress level is approximately 50%. There is no sharp yield stress. Thus, the material is resilient or plastically deformable at stress levels up to about 5 kg/cm$^2$ becoming progressively permanently stretched at greater stress levels.

The above ingredients were suspended in approximately 500 milliliters of isoparaffinic solvent and agitated in a Waring blender for three minutes. Mixed ingredients were rapidly poured into a Buchner funnel and suction applied for one minute. The filter cake thereby obtained was placed within the platens of a heated press (150° F) and compressed under 500 pounds per square inch for one minute. A level of isoparaffinic solvent within the product at this stage was measured to be 11.5 weight percent. The product was then rolled according to the procedure described under Step D above with roll temperature of 120° F. The rolled stock was dried for 24 hours, 300° F and then compression sintered under 500 psi for five minutes at 660° F. This product is now suitable for lamination to fluorinated ethylene propylene polymer film according to the precedure hereinafter described. The lamination in this case may be accomplished in a heated platen press at 570° F under ten pounds per square inch pressure for five minutes.

While the foregoing sets forth the preferred material composition of the present invention other materials may be used. Any chemically stable perfluorinated high polymer such as polyhexafluoropropylene, or a copolymer of hexafluoropropylene and tetrafluoroethylene which is commercially available as the TEFLON FEP resin from Du Pont is believed to be suitable base material from which a porous implantable material may be formed. Other suitable materials are high molecular weight polyethylene containing no additives, polyester polymers such as polyethylene terephthalate. The preferred materials to be used have the following charateristics; they are bio-compatible (suitable for in vivo implantation), they are not subject to chemical migration when implanted, they are stable for autoclaving, they allow development of porosity for ingrowth and they are resilient.

For example polyester fibers as sold by Du Pont Company under their mark DACRON can be used. A typical formation includes 4.5 grams of graphite fibers, 2.52 grams of the above-mentioned polyester fiber flock, 2.76 grams of TEFLON TFE-6 resin and 52.1 grams of salt. This formulation was mixed, filtered and otherwise processed in accordance with the steps set forth above except that the compression sintering was carried out for one minute at 530° F.

While it is preferred that the additive is a carbon fiber, a combination of filamentary and powdered carbon or metal (which metals are suitable for implantation), or other fibers such as ceramic, may be used as additives provided the internal surface tension of the material remains sufficiently high to be highly blood wettable and therefore suitable for ingrowth of tissues.

Following are examples of other material compositions of the present invention:

| Ingredients | Volume % | Grams |
| --- | --- | --- |
| Salt, NaCl | 80% | 6.20g |
| Zirconia Fibers | 10% | 2.00g |
| Teflon TFE Fiber | 6% | 0.50g |
| Teflon TFE - 6 Resin | 4% | 0.33g |

The zirconia fibers used were obtained from the Mond Division of Imperial Chemical Industries and are sold under the trademark SAFFIL. They are based on zirconium oxide. The fiber diameter is 3 ± 2 micra.

| Ingredients | Volume % | Grams |
| --- | --- | --- |
| Salt, NaCl | 80% | 6.20g |
| Alumina Fibers | 10% | 1.00g |
| Teflon TFE Fiber | 6% | 0.50g |
| Teflon TFE - 6 Resin | 4% | 0.33g |

The alumina fibers used were SAFFIL alumina fibers based on aluminum oxide.

| Ingredients | Volume % | Grams |
|---|---|---|
| Salt, NaCl | 80% | 34.72 |
| Whiskers, SiC, $Al_2O_3$ | 10% | 7.2 |
| Teflon TFE Fiber | 6% | 2.76 |
| Teflon TFE - 6 Resin | 4% | 1.84 |

| Ingredients | Volume % | Grams |
|---|---|---|
| Salt, NaCl | 80% | 34.72 |
| Whiskers, SiC, $Al_2O_3$ | 8% | 5.76 |
| Teflon TFE Fiber | 7% | 3.22 |
| Teflon TFE - 6 Resin | 5% | 2.3 |

The single crystal filaments (whiskers) of silicone carbide and aluminum oxide may be purchased from General Technology Corporation, Reston, Va. as Type 6B and falling in the range from 2 to 30 micra in diameter and from 20 to 1000 micra in length.

| Ingredients | Volume % | Grams |
|---|---|---|
| Salt, NaCl | 80% | 34.72 |
| Stainless Steel Wire | 10% | 16.0 |
| Teflon TFE Fiber | 6% | 2.76 |
| Teflon TFE - 6 Resin | 4% | 1.84 |

| Ingredients | Volume % | Grams |
|---|---|---|
| Salt, NaCl | 80% | 34.72 |
| Stainless Steel Wire | 8% | 12.8 |
| Teflon TFE Fiber | 7% | 3.22 |
| Teflon TFE - 6 Resin | 5% | 2.2 |

The stainless steel wire used was approximately one-fourth inch (5 to 6 mm) in length and 0.005 inches (0.127 mm) in diameter.

| Ingredients | Volume % | Grams |
|---|---|---|
| Salt, NaCl | 80% | 34.72 |
| Vitreous Carbon Fiber | 10% | 3.0 |
| Polyester Fiber | 10% | 2.76 |

| Ingredients | Volume % | Grams |
|---|---|---|
| Salt, NaCl | 80% | 34.72 |
| Vitreous Carbon Fiber | 10% | 3.0 |
| Polyaramide Fiber | 10% | 2.76 |

The polytetrafluoroethylene fiber, polyester fiber and the polyaramide fibers were obtained from DuPont Company of Wilmington, Del. under the trademarks Teflon, Dacron and Nomex, respectively.

Further, it has been found that in the above polyester and polyaramide compositions extensive mixing is used to provide a complete blending of the components to avoid the production of composition in which not all of the fibers were completely integrated into the structure. To avoid extensive mixing, the following composition was made:

| Ingredients | Volume % | Grams |
|---|---|---|
| Salt, NaCl | 80% | 34.72 |
| Vitreous Carbon Fiber | 10% | 3.0 |
| Polyester Fiber | 6% | 1.65 |
| Teflon TFE - 6 Resin | 4% | 1.84 |

As can be seen this composition is substantially the same as the previously described composition with the addition of the polytetrafluoroethylene resin. This resin is believed to act as a mixing adjuvant allowing the polyester fibers and the carbon fibers to be mechanically mixed or blended with the salt and a liquid organic solvent to form a substantially homogeneous mixture. While improved compositions may be produced without the inclusion of such mixing adjuvant, its inclusion greatly simplifies the productiion of a suitable composition.

Also, a high molecular weight polyethylene resin such as the resin sold by Hercules, Inc., of Wilmington, Del., under the trademark Hyfax 1900 was used with the polyester and polyaramide fiber compositions in place of the polytetrafluoroethylene and as a strengthening ingredient. Such compositions were sintered at a temperature of 450° F.

From the foregoing it may be seen that the improved composition of the present invention may be of a wide variety of materials provided such materials are biocompatible and produce a fibrous, porous structure in which at least a portion of the fibers have a critical surface tension within the preferred range so as to be blood wettable and thereby assure the promotion of ingrowth of living tissue when implanted in a human body.

The composition includes a fiber which supplies the critical surface tension and a bond component which bonds the fibers into the pliable, resilient and porous composition with a suitable material such as salt providing the degree of porosity by initially being incorporated in the structure and being leached therefrom after the sintering.

As has been shown the fiber components which supply the blood wettability may be selected from the group of carbonaceous fibers, stainless steel fibers, silicon carbide fibers, aluminum oxide fibers, zirconia fibers and other material fibers which are biocompatible, have the required high critical surface tension and may be sterilized in conformity with accepted operating room procedures.

The bonding material may be polytetrafluoroethylene, polyester, polyethylene, polyaramide, and other materials which are biocompatible, will bond the fiber materials and may be sterilized in conformity with accepted operating room procedures.

The improved composition of material of the present invention forms a three dimensional structure which is substantially isotropic or has substantially uniform characteristics in all three dimensions. The composition of material further has a sufficient resiliency and distensibility so that on implantation the tissues growing therein are subjected to the forces at the site of the implant and will tend to mature into the type of tissue needed at such location responsive to such forces.

In all of the above compositions which differed from the preferred composition, the previously described steps in the method of producing the preferred composition were used with only a variation in the temperatures used to accommodate the different bonding materials. For example, sintering temperatures for the polyester bonding material would be approximately 500° F. and approximately 650° F. for the polyaramide material.

The stabilization of orthopedic appliances can be accomplished by the bonding of the material of the present invention to the fixation portion of the appliance. A typical example of this stabilization is the bonding of the ingrowth promoting material to the stem of a metal femoral head prosthesis. Also such material can be added to the convex surface of a metal acetabular prosthesis. The bonding to a metal prosthesis may be accomplished preferably by bonding a thin layer of fluorinated ethylenepropylene (Du Pont TEFLON FEP) to the material before the major portion of the salt is leached therefrom. The salt on such surface is removed before bonding the bonding layer thereto. This may be accomplished by floating the material on distilled water for a short period of time to assure that the bonding material is bonded to the composition of material. Such bonding layer provides the bond to the metal prosthesis.

In bonding the material of the present invention to a metal appliance or to suitable wear material, it is preferred that the material with its layer of bonding material bonded thereto be placed in a silicone rubber mold with the metal appliance or wear material. The silicone rubber mold is placed in a stainless steel container in a snug fit and is positively restrained therein by suitable restraining devices. The mold is placed in an oven in which it is slowly heated (100° F per hour) to between 560° F and 620° F and then the mold is held at such temperature for a period of from one to six hours before cooling at the same rate as the heating rate. Alternatively the mold may be directly placed in an oven held at the range 560°–620° F. Over this heating cycle the material is bonded by the bonding material to the metal appliance or the wear material and is formed to the desired shape of the appliance such as surrounding the stem of a femoral head prosthesis. After the molding step, the salt is leached from the material by emersion of the prosthesis in distilled water.

For molding the growth promoting material into special shapes it is preferred that the stock material be molded prior to sintering by pressure and temperatures up to 400° F. Complicated shapes can be produced to duplicate the anatomy of resected joint bone and tissue.

The stabilization of orthopedic appliances with the tissue ingrowth promoting material results from ingrowth of tissue into the material rather than by sequestration of the appliance. Actual animal implants have shown the rapid development of loose, immature, collagen throughout the material (3000 microns in radial dimension) during the third, fourth and fifth weeks. At the same time dense mature collagen was seen to develop from the periphery of the implant towards the center. There is a distinct trend that the depth of mature collagen increases with time following implantation. It appears that the relatively rapid development of loose, immature collagen proceeds in situ as a direct consequence of the hematoma which was seen to develop within the implant materials at implantation. Such animal implants resulted in linear rates of mature collagen development between 40 and 120 microns per week.

Partial and complete joint prosthesis devices are believed to be possible by the use of the improved composition of material of the present invention. The building blocks of such composite structures include the composition of material, previously described a bonding material such as the Du Pont TEFLON FEP material, metallic prosthesis elements, and a wear material including material of Du Pont TEFLON TFE resin with inert material and fibrous material embodied therein as hereinafter described.

With those building blocks the growth promoting material of the present invention may be added to usual metal prosthetic devices for stabilization of such devices and may be used with other material for partial or total joint replacement. Typical examples of the stabilizing use of such materials would be femoral head device with the growth promoting material bonded to the stem of a metal prosthesis. An acetabular cup prosthesis with the growth promoting material bonded to the convex side thereof would be another type of device which would be stabilized by the growth of tissue into the material bonded to the cup. Another possible use of the growth promoting material for stabilization could be in single teeth or total dentures stabilized with respect to gum tissue and mandibular bone.

A partial joint prosthesis can be accomplished on a knee by utilizing the growth promoting material positioned on the tibial plateau after the minimum necessary resection with the wear material (hereinafter described) bonded to the top of the growth promoting material by the usual bonding material. This laminated structure is secured in position in any suitable manner such as by letting the growth promoting material extend beyond the articulating surface laterally and medially for suturing at implantation. A similar implant to the femoral portion of the knee to mate with the tibial implant may be used to thereby provide a complete joint prosthesis.

With partial or complete joint prostheses it is important that the implanted device have uniform fixation, appropriate friction and wear characteristics, and approximate the bulk and strength of the resected tissue. All materials should be bio-compatible, have no chemical migration when implanted and be stable for autoclaving. The composite structure for partial or complete joint prosthesis should approximate the resilience of the normal joint. Where additional resilience is desired a layer of medical grade silicone rubber may be added between the growth material and the wear material.

Another possible human implantation use of the growth promoting material of the present invention is as prosthetic tendons. For such prosthetic tendons the growth promoting material is bonded to the ends of a strip of Du Pont TEFLON FEP of appoximately the desired tendon length. The growth promoting material at the ends serves to form a bond to the stump of the excised tendon close to the point at which the tendon enters the muscle at one end and to the bone at the other end. Other materials may be used as the strip material such as silicone Silastic 372. Such materials cause the formation of membranous capsule of tissue (a tunnel) through which the tendon material may slide during motion.

It is preferred in tendon replacement that the material used not have any appreciable stretch and therefore a preferred composition of material would be a lamination of a high strength fabric made of glass fibers or polytetrafluoroethylene fibers between or encapsulated within the aforementioned Du Pont TEFLON FEP.

A factor in the use of the growth promoting material which facilitates its use if it is to be bonded to other materials is to dissolve the salt in the material only in the surface to be bonded until the bonding is complete. This surface leaching has been accomplished by floating the flat material with the salt therein on distilled water for a short period of time such as twenty minutes. The bonding is then completed and any molding accomplished on the laminated structure to prepare it for implantation. When the molding is completed the remainder of the salt is dissolved from the material.

The wear material which has been found suitable for implantation as hereinbefore described has a composition of more than 15 percent by volume to 50 percent by volume carbon fibers and particles and less than 85 percent by volume to 50 percent by volume of polytetrafluoroethylene resin such as is marketed by Du Pont as their TFE resin.

The preferred composition of material for implantation is 40 percent by volume fibrous carbon or graphite and 60 percent by volume of the TFE fluorocarbon polymer. A composition which has exhibited excellent wear properties and low friction is one containing 30 percent by volume fibrous carbon or graphite, 10 percent by volume particulate carbon or graphite and 60 percent by volume TFE polymer. Generally it is preferred that the ratio of total fibrous and particulate carbon to fibrous carbon be from 1 to 1 to 5 to 1.

The wear composition is prepared by mixing the resin and carbon or graphite with a suitable solvent such as isoparaffinic hydrocarbon in a high speed, high shear mixer. The amount of solvent is adjusted to the size of the mixer. For example, in a mixer of 500 milliliters, 375 milliliters of solvent is used for dry ingredients weighting approximately 50 grams. Mixing is carried out until a complete uniform slurry is produced.

The mixed slurry is filtered. The filtration is preferred to be by vacuum filter such as a Buchner funnel, and should proceed until the residual solvent left in the filter cake is less than approximately 20 percent by weight.

Following filtration, the filter cake is placed between the platens of a heated press and is compressed at levels of from 500 to 3,000 psi and at a temperature between 100° and 250° F. for periods from one to five minutes. The conditions are adjusted so that the solvent level after compression is between six and ten percent by weight.

Next, the compressed filter cake is run through the nip of heated rolls which are heated to a temperature between 100° F and 250° F. This temperature is adjusted to the particular volatility of the solvent. The thickness of the cake is reduced in decrements of approximately 20/1000ths of an inch to a thickness between 20/1000ths and 80/1000ths of an inch.

When the desired thickness is reached, the temperature of the rolls is elevated to between 320° and 360° F and the thickness of the material during each subsequent pass is reduced to one-half its thickness. To maintain the desired thickness, the sheet of material is doubled after each pass and then is run through the next pass at 90° to the previous pass. This procedure may be carried out from four to eight times depending on the apparent toughness of the product at a given stage of rolling.

When rolling is completed, the material is sintered at a temperature from 610° F to 680° F for periods from thirty minutes to several hours depending on the thickness of the stock. It should be noted that if the product contains residual solvent which is slow to evaporate, extended periods of drying at temperatures from 300° to 400° F may be required.

The preferred form of such wear material includes the fibrous carbon. This material has improved wear properties and low friction. It is believed that the reason for such improved properties results from the orientation of the carbon fibers to a position generally parallel to the wear surface. In such position, the carbon fibers would not have a tendency to break off and thereby create an extreme wear problem and further since the carbon fibers have a low coefficient of friction, the exposure of the carbon fibers on the wear surface would not cause a drastic increase in friction as might be expected with other materials.

The improved growth promoting material of the present invention has a surface tension above 35 dynes per centimeter on a scale extending from 20 to 80 dynes per centimeter.

The foreoing disclosure and description of the invention are illustrative and explanatory thereof, and various changes in the size, shape and materials, as well as in the details of the illustrated construction, may be made within the scope of the appended claims without departing from the spirit of the invention.

What is claimed is:

1. A composition of material suitable for in vivo implantation comprising
    a resilient, fibrous, porous structure,
    at least a portion of the fibers of said structure having a critical surface tension above 35 dynes per centimeter on a scale extending from 20 to 80 dynes per centimeter,
    said structure including means for bonding said fibers into the porous structure having substantial interconnected spaces between the fibers, and
    said fibers and said bonding means both being biocompatible.
    said structure having sufficient resiliency and distensibility when implanted to develop the type of ingrowth tissue needed at the implant location responsive to the mechanical forces at the implant site.

2. A composition of material according to claim 1 wherein said fibers are carbon fibers.

3. A composition of material according to claim 1 wherein the porosity of said structure includes both spheroidal and dendritic spaces.

4. A composition of material according to claim 1, including
    a wear material bonded to one surface of said structure.

5. A composition of material according to claim 4 wherein said wear material comprises
    carbon fibers, and
    polytetrafluoroethylene resin sintered with said carbon fibers to retain said fibers with respect to each other.

6. A compositon of material according to claim 1 wherein said fibers are carbonaceous fibers.

7. A composition of material suitable for in vivo implantation comprising
a fibrous, porous structure,
at least a portion of the fibers of said structure having a critical surface tension above 35 dynes per centimeter,
said structure including means for bonding said fibers into the porous structure having substantial interconnected spaces between the fibers,
said fibers and said bonding means both being biocompatible,
said fibers being carbonaceous fibers, and
said bonding means including polytetrafluoroethylene resin and fibers.

8. A composition of material suitable for in vivo implantation comprising,
a fibrous, porous structure,
at least a portion of the fibers of said structure having a critical surface tension above 35 dynes per centimeter on a scale extending from 20 to 80 dynes per centimeter,
said structure including means for bonding said fibers into the porous structure having substantial interconnected spaces between the fibers, and
said fibers and said bonding means both being biocompatible,
said fibers being selected from a group consisting of carbonaceous fibers, stainless steel fibers, silicone carbide whiskers, aluminum oxide whiskers and zirconia fibers,
said bonding means including polytetrafluoroethylene fibers.

9. A composition according to claim 8 wherein the porosity of the bonded structure includes both dendritic and spheroidal voids which are interconnected.

10. A composition according to claim 8 wherein the bonded structure has at least 60 percent void space.

11. A composition according to claim 8 wherein said bonding means is polytetrafluoroethylene.

12. A composition according to claim 8 including a bonding resin bonded to one surface of said structure, said bonding resin being suitable for bonding said structure to other resin structures and to metal.

13. A composition according to claim 8 including a leachable substance in said structure except at the surface to which said bonding resin is bonded so that when leached out of said structure the desired porosity is provided.

14. A composition of material according to claim 1 including
a soluble material included in said structure so that when leached therefrom the spaces occupied by said soluble material define at least a substantial portion of the porosity of said structure.

15. A composition of material suitable for in vivo implantation comprising,
a fibrous, porous structure,
at least a portion of the fibers of said structure having a critical surface tension above 35 dynes per centimeter on a scale extending from 20 to 80 dynes per centimeter,
said structure including means for bonding said fibers into the porous structure having substantial interconnected spaces between the fibers, and
said fibers and said bonding means both being biocompatible, a soluble sodium chloride included in said structure so that when leached therefrom the spaces occupied by said sodium chloride define at least a substantial portion of the porosity of said structure.

16. A composition of material according to claim 15 wherein
said sodium chloride is reagent grade crystals having a size from 10 to 600 microns.

17. A composition of material according to claim 14 including
one surface of said structure being free of said soluble material and having a bonding material bonded thereto.

18. A composition of material suitable for in vivo implantation comprising,
a fibrous, porous structure,
at least a portion of the fibers of said structure having a critical surface tension above 35 dynes per centimeter on a scale extending from 20 to 80 dynes per centimeter,
said structure including means for bonding said fibers into the porous structure having substantial interconnected spaces between the fibers, and
said fibers and said bonding means both being biocompatible,
a soluble material included in said structure so that when leached therefrom the spaces occupied by said soluable material define at least a substantial portion of the porosity of said structure,
one surface of said structure is free of said soluble material and having a fluorinated ethylene propylene polymer bonding material bonded thereto.

19. A composition of material suitable for an in vivo implantation comprising
a fibrous, porous structure,
at least a portion of the fibers of said structure having a critical surface tension above 35 dynes per centimeter on a scale extending from 20 to 80 dynes per centimeter,
said structure including means for bonding said fibers into the porous structure having substantial interconnected spaces between the fibers,
said fibers and said bonding means both being biocompatible,
a soluble material included in said structure so that when leached therefrom the spaces occupied by said soluble material define at least a substantial portion of the porosity of said structure,
said structure includes carbon fibers in the range from 4 to 20 percent by volume,
polytetrafluoroethylene fibers in the range from 4 to 10 percent by volume,
polytetrafluoroethylene fibers in the range from 2 to 10 percent by volume, and
said soluble material in the range from 60 to 90 percent by volume.

20. A composition of material suitable for in vivo implantation comprising,
a fibrous, porous structure,
at least a portion of the fibers of said structure having a critical surface tension above 35 dynes per centimeter on a scale extending from 20 to 80 dynes per centimeter,
said structure including means for bonding said fibers into the porous structure having substantial interconnected spaces between the fibers, and
said fibers and said bonding means both being biocompatible,
a soluble material included in said structure so that when leached therefrom the spaces occupied by said soluable material define at least a substantial portion of the porosity of said structure, and wherein said structure includes ten percent by volume carbon fibers, six percent by volume resin fibers, four percent by volume resin particles, and eighty percent by volume soluble material.

21. A composition of material suitable for in vivo implantation and adapted to promote ingrowth of tissue, comprising
a plurality of resin fibers,
a plurality of carbon fibers, and
said resin fibers bonding said carbon fibers into a structure having substantial porosity,
said resin fibers and carbon fibers being biocompatible,
the bond of said resin being at relatively small points whereby substantial portions of the surface of said carbon fibers are exposed.

22. An appliance for implantation comprising a high strength fabric encapsulated within an elongated element of fluorinated ethylenepropylene polymer, and
a composition of material according to claim 1 bonded to each end of elongated element.

23. An appliance for implantation comprising
a metal element, and
a composition of material according to claim 1 bonded thereto.

24. An appliance according to claim 23 wherein said composition is bonded to said metal element by means of a bonding material.

25. An appliance according to claim 24 wherein said bonding material is a fluorinated ethylenepropylene polymer.

26. An appliance according to claim 23 wherein said composition includes a wear material bonded to the outer surface thereof.

27. An appliance according to claim 26 wherein said wear material comprises carbon fibers and polytetrafluoroethylene resin sintered with said carbon fibers to retain said fibers with respect to each other.

28. The method of promoting ingrowth of normal body tissue in an implantable material which comprises implanting a composition of material comprising
a resilient, fibrous, porous structure,
at least a portion of the fibers of said structure having a critical surface tension above 35 dynes per centimeter on a scale extending from 20 to 80 dynes per centimeter,
said structure including means for bonding said fibers into the porous structure having substantial interconnected spaces between the fibers, and
said fibers and said bonding means both being biocompatible,
said structure having sufficient resiliency and distensibility when implanted to develop the type of ingrowth tissue needed at the implant location responsive to the mechanical forces at the implant site.

29. The method of stabilizing an orthopedic appliance which comprises bonding a composition according to claim 12 to the fixation portion of said appliance.

30. The method according to claim 29 wherein the bonding resin of said composition is a fluorinated ethylenepropylene polymer.

31. The method of stabilizing a dental implant which comprises bonding a composition according to claim 12 to said implant.

32. A composition according to claim 1 wherein
said fibers are selected from a group consisting of carbonaceous fibers, stainless steel fibers, silicone carbide whiskers, aluminum oxide whiskers and zirconia fibers.

33. A composition according to claim 1 wherein
said bonding means is selected from the group of a perfluorinated polymer, a polyethylene, a polyester and a polyaramide.

34. A composition of material suitable for in vivo implantation comprising
a resilient, fibrous, porous structure,
at least a portion of the fibers of said structure having a critical surface tension above 35 dynes per centimeter on a scale extending from 20 to 80 dynes per centimeter,
said structure including means for bonding said fibers into the porous structure having substantial interconnected spaces between the fibers,
said structure having sufficient resiliency and distensibility when implanted to develop the type of ingrowth tissue needed at the implant location responsive to the mechanical forces at the implant site,
said fibers and said bonding means both being biocompatible, and
said fibers are carbonaceous material and said bonding means includes one of a perfluorinated polymer, polyethylene and a polyester.

35. A composition of material comprising
a resilient, fibrous, porous structure,
at least a portion of the fibers of said structure having a critical surface tension above 35 dynes per centimeter on a scale extending from 20 to 80 dynes per centimeter,
said structure including means for bonding said fibers into the porous structure having substantial interconnected spaces between the fibers, and
said fibers and said bonding means both being biocompatible,
said structure having a porosity in the range from 60 to 90 percent of the volume of said structure.

* * * * *

UNITED STATES PATENT OFFICE
CERTIFICATE OF CORRECTION

Patent No. 3,992,725      Dated November 23, 1976

Inventor(s)   Charles A. Homsy

It is certified that error appears in the above-identified patent and that said Letters Patent are hereby corrected as shown below:

Column 3, line 12, the introduction to the table insert -- The preferred range of composition is as follows: --.

Column 14, line 51, "fibers" should read -- resin --.

Signed and Sealed this

Eighth Day of March 1977

[SEAL]

Attest:

RUTH C. MASON
*Attesting Officer*

C. MARSHALL DANN
*Commissioner of Patents and Trademarks*